(12) United States Patent
Sanuki et al.

(10) Patent No.: US 9,643,942 B2
(45) Date of Patent: May 9, 2017

(54) METHOD FOR MANUFACTURING 1,1-DISUBSTITUTED HYDRAZINE COMPOUND

(71) Applicant: ZEON CORPORATION, Chiyoda-ku, Tokyo (JP)

(72) Inventors: Kanako Sanuki, Tokyo (JP); Kumi Okuyama, Tokyo (JP)

(73) Assignee: ZEON CORPORATION, Chiyoda-ku, Tokyo (JP)

( * ) Notice: Subject to any disclaimer, the term of this patent is extended or adjusted under 35 U.S.C. 154(b) by 0 days.

(21) Appl. No.: 15/119,191

(22) PCT Filed: Feb. 24, 2015

(86) PCT No.: PCT/JP2015/055122
§ 371 (c)(1),
(2) Date: Aug. 16, 2016

(87) PCT Pub. No.: WO2015/129654
PCT Pub. Date: Sep. 3, 2015

(65) Prior Publication Data
US 2017/0008862 A1    Jan. 12, 2017

(30) Foreign Application Priority Data
Feb. 28, 2014    (JP) .................. 2014-039673

(51) Int. Cl.
*C07D 277/82*    (2006.01)
(52) U.S. Cl.
CPC .................. *C07D 277/82* (2013.01)
(58) Field of Classification Search
CPC .................................................. C07D 277/82
See application file for complete search history.

(56) References Cited

U.S. PATENT DOCUMENTS

2014/0142266 A1    5/2014    Sakamoto et al.

FOREIGN PATENT DOCUMENTS

| JP | S61151181 A | 7/1986 |
| WO | 2012147904 A1 | 11/2012 |

OTHER PUBLICATIONS

Haviv et al., Journal of Medicinal Chemistry, 1988, 31(9), pp. 1719-1728.*
Sep. 6, 2016. International Preliminary Report on Patentability issued in the International Patent Application No. PCT/JP2015/055122.

* cited by examiner

*Primary Examiner* — Laura L. Stockton
(74) *Attorney, Agent, or Firm* — Kenja IP Law PC

(57) ABSTRACT

This method for a manufacturing a 1,1-disubstituted hydrazine compound represented by a formula (II) involves reacting a hydrazino compound represented by a formula (I) with a compound represented by a formula: R-Hal in an aprotic polar solvent in the presence of a base selected from an alkali metal hydroxide and alkaline-earth metal hydroxide in an amount of 1.0 to 3.0 equivalents based on the hydrazino compound. In the formulae, X represents an oxygen atom, a sulfur atom, —$CH_2$— or the like, and each of $R^X$ represents a hydrogen atom, a halogen atom, an alkyl group having 1 to 6 carbon atoms, a cyano group, a nitro group, a fluoroalkyl group having 1 to 6 carbon atoms, an alkoxy group having 1 to 6 carbon atoms or the like. An arbitrary C—$R^X$ that forms the ring is optionally substituted with a nitrogen atom. Hal represents a chlorine atom, a bromine atom, or an iodine atom, and R represents a substituted or unsubstituted organic group having 1 to 12 carbon atoms.

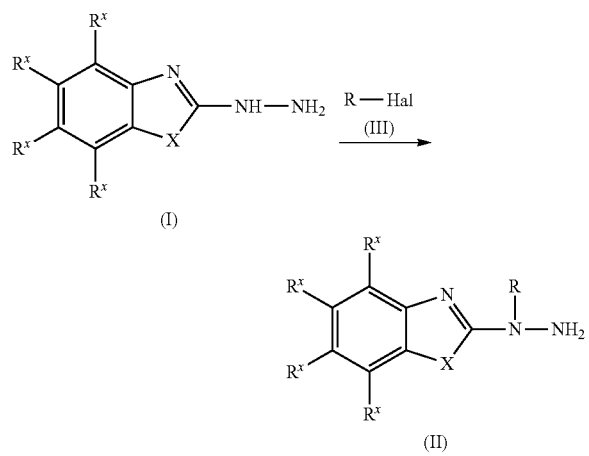

10 Claims, No Drawings

METHOD FOR MANUFACTURING 1,1-DISUBSTITUTED HYDRAZINE COMPOUND

TECHNICAL FIELD

The present invention relates to a method that industrially advantageously produces a 1,1-disubstituted hydrazine compound (that is useful as a production intermediate) at low cost in high yield.

A 1,1-disubstituted hydrazine compound (e.g., 1,1-disubstituted hydrazinobenzothiazole) is a compound that is useful as an industrial raw material and an intermediate for producing a drug, an agricultural chemical, and the like.

The following methods are known as a method for producing a 1,1-disubstituted hydrazine compound.

(a) Patent Literature 1 discloses that 2-(1-methylhydrazino)benzothiazole is "obtained by reacting 2-chlorobenzothiazole with methylhydrazine, or converting 2-(N-methylamino)benzothiazole or the like into a nitroso compound using nitrous acid, and reducing the nitroso compound using a reducing agent, for example". However, Patent Literature 1 does not disclose the details of the production method, the reaction yield, and the like.

(b) Patent Literature 2 discloses synthesis examples of various 1,1-disubstituted hydrazinobenzothiazoles in which hydrazinobenzothiazole is used as a raw material, and potassium carbonate, cesium carbonate, or hexamethyldisilazane is used as a base.

Since hydrazinobenzothiazole that is used for the production method disclosed in Patent Literature 2 is produced industrially and readily available, hydrazinobenzothiazole is a raw material that is advantageous for industrial production. However, the method disclosed in Patent Literature 2 has a problem in that a competing reaction proceeds when a substituent is introduced directly into hydrazinobenzothiazole, whereby a 1,2-disubstituted hydrazinobenzothiazole is produced as a by-product. This makes it difficult to obtain the target product in high yield. Moreover, since it is necessary to use expensive cesium carbonate or the like as the base in large excess, the production cost increases. Since the synthesis method disclosed in Patent Literature 2 requires column purification after separation, it is difficult to produce the target product on an industrial scale.

Specifically, since the known method for producing a 1,1-disubstituted hydrazinobenzothiazole includes effecting the reaction using a large amount of expensive reagent, and removing a 1,2-disubstituted hydrazinobenzothiazole or the like (i.e., by-product) through column purification, it is very difficult to implement the method on an industrial scale in terms of cost.

CITATION LIST

Patent Literature

Patent Literature 1: JP-A-61-151181
Patent Literature 2: WO2012-147904 (US2014/0142266A1)

SUMMARY OF INVENTION

Technical Problem

The invention was conceived in view of the above situation. An object of the invention is to provide a method that synthesizes a 1,1-disubstituted hydrazine compound (e.g., 1,1-disubstituted hydrazinobenzothiazole) at low cost using inexpensive and readily-available hydrazinobenzothiazole or the like as a raw material, and using an inexpensive reagent.

Solution to Problem

The inventors of the invention conducted extensive studies in order to solve the above problem. As a result, the inventors found that the target 1,1-disubstituted hydrazine compound represented by the following formula (II) can be produced in high yield by reacting a compound represented by the following formula (I) with a halogen compound represented by the following formula (III) in an aprotic polar solvent in the presence of a specific amount of base selected from an alkali metal hydroxide and alkaline-earth metal hydroxide. This finding has led to the completion of the invention.

One aspect of the invention provides the following method for producing a 1,1-disubstituted hydrazine compound (see (1) to (10)).

(1) A method for producing a 1,1-disubstituted hydrazine compound including reacting a hydrazino compound represented by the following formula (I) with a compound represented by the formula (III): R-Hal in an aprotic polar solvent in the presence of a base selected from an alkali metal hydroxide and alkaline-earth metal hydroxide in an amount of 1.0 to 3.0 equivalents based on the hydrazino compound,

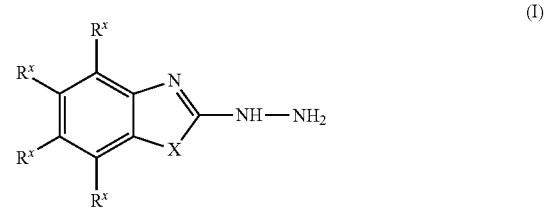

wherein Hal represents a chlorine atom, a bromine atom, or an iodine atom, and R represents a substituted or unsubstituted organic group having 1 to 12 carbon atoms, wherein X represents an oxygen atom, a sulfur atom, —$CH_2$—, —$CHR^1$—, —$CR^1R^2$—, or —$NR^1$—, wherein each of $R^1$ and $R^2$ independently represents a hydrogen atom, or a substituted or unsubstituted alkyl group having 1 to 10 carbon atoms, and each of $R^X$ represents a hydrogen atom, a halogen atom, an alkyl group having 1 to 6 carbon atoms, a cyano group, a nitro group, a fluoroalkyl group having 1 to 6 carbon atoms, an alkoxy group having 1 to 6 carbon atoms, an alkylthio group having 1 to 6 carbon atoms, a monosubstituted amino group, a disubstituted amino group, or —C(=O)—O—$R^3$, wherein represents a hydrogen atom, or a substituted or unsubstituted alkyl group having 1 to 10 carbon atoms, provided that $R^X$ are identical to or different from each other, and an arbitrary C—$R^X$ that forms the ring is optionally substituted with a nitrogen atom, the 1,1-disubstituted hydrazine compound being represented by the following formula (II),

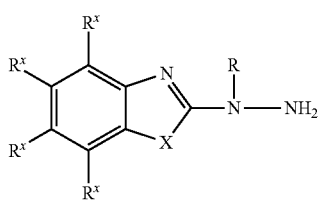

wherein X, R, and $R^x$ are the same as defined above.

(2) The method according to (1), further including adding a protic solvent to the reaction mixture obtained by the reaction to effect direct crystallization.

(3) The method according to (2), wherein the protic solvent is water.

(4) The method according to any one of (1) to (3), wherein the compound represented by the formula (I) is the compound represented by the formula (I) in which each of $R^x$ is a hydrogen atom.

(5) The method according to any one of (1) to (4), wherein the compound represented by the formula (I) is the compound represented by the formula (I) in which X is a sulfur atom.

(6) The method according to any one of (1) to (5), wherein the compound represented by the formula (III): R-Hal is the compound represented by the formula (III) in which R is a substituted or unsubstituted alkyl group having 1 to 12 carbon atoms.

(7) The process according to any one of (1) to (6), wherein the base is an alkali metal hydroxide.

(8) The process according to any one of (1) to (7), wherein the base is sodium hydroxide or potassium hydroxide.

(9) The process according to any one of (1) to (8), wherein the base is used in an amount of 1.0 to 2.0 equivalents based on the hydrazino compound.

(10) The method according to any one of (1) to (9), wherein the aprotic polar solvent is at least one aprotic polar solvent selected from the group consisting of N,N-dimethylformamide, N,N-dimethylacetamide, N-methylpyrrolidone, acetonitrile, 1,3-dimethyl-2-imidazolidinone, and dimethyl sulfoxide.

Note that the expression "substituted or unsubstituted" used herein in connection with a group or the like means that the group or the like is unsubstituted, or substituted with a substituent.

Advantageous Effects of Invention

The method according to one aspect of the invention can produce a 1,1-disubstituted hydrazine compound (e.g., 1,1-disubstituted hydrazinobenzothiazole) in high yield by introducing a substituent directly into hydrazinobenzothiazole or the like (that is produced industrially and readily available) used as a raw material with high reaction selectivity using only an inexpensive reagent.

Specifically, the method according to one aspect of the invention can produce the target compound (II) (1,1-disubstituted hydrazine compound) in high yield with high reaction selectivity without producing a 1,2-disubstituted hydrazine compound shown below as a by-product.

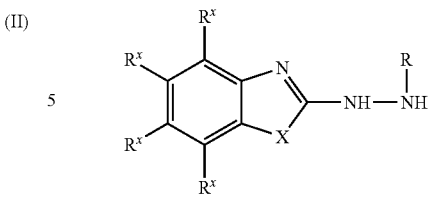

When direct crystallization is effected without purification, a high-purity target product can be obtained by short-step synthesis in high yield.

DESCRIPTION OF EMBODIMENTS

The invention is described in detail below.

A method for producing a 1,1-disubstituted hydrazine compound according to one embodiment of the invention includes reacting a hydrazino compound represented by the following formula (I) (hereinafter may be referred to as "hydrazino compound (I)") with a compound represented by the formula (III): R-Hal (hereinafter may be referred to as "compound (III)") in an aprotic polar solvent in the presence of a base selected from an alkali metal hydroxide and alkaline-earth metal hydroxide in an amount of 1.0 to 3.0 equivalents based on the hydrazino compound, the 1,1-disubstituted hydrazine compound being represented by the following formula (II).

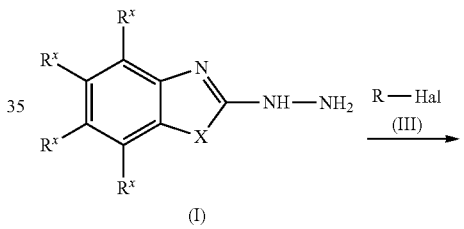

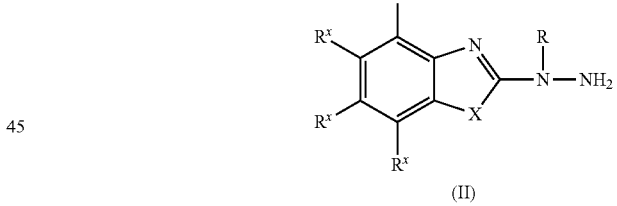

wherein X represents an oxygen atom, a sulfur atom, $-CH_2-$, $-CHR^1-$, $-CR^1R^2-$, or $-NR^1-$.

Note that each of $R^1$ and $R^2$ independently represents a hydrogen atom, or a substituted or unsubstituted alkyl group having 1 to 10 carbon atoms.

Examples of the alkyl group having 1 to 10 carbon atoms that forms the substituted or unsubstituted alkyl group having 1 to 10 carbon atoms represented by $R^1$ and $R^2$ include a methyl group, an ethyl group, an n-propyl group, an isopropyl group, an n-butyl group, a sec-butyl group, a t-butyl group, an n-pentyl group, an isopentyl group, a neopentyl group, an n-hexyl group, an isohexyl group, a 3-heptyl group, an n-octyl group, an n-nonyl group, an n-decyl group, and the like.

Examples of a substituent that may substitute the alkyl group having 1 to 10 carbon atoms include a halogen atom such as a fluorine atom and a chlorine atom; a cyano group; a substituted amino group such as a methylamino group and a dimethylamino group; an alkoxy group having 1 to 6 carbon atoms, such as a methoxy group and an ethoxy group; a nitro group; an aryl group such as a phenyl group, a 1-naphthyl group, and a 2-naphthyl group; a cycloalkyl group having 3 to 8 carbon atoms, such as a cyclopropyl group and a cyclopentyl group; a hydroxyl group; and the like.

It is preferable that X be an oxygen atom, a sulfur atom, or —CH$_2$—, more preferably an oxygen atom or a sulfur atom, and particularly preferably a sulfur atom, since the advantageous effects of the invention can be more easily achieved.

Each of $R^X$ represents a hydrogen atom, a halogen atom (e.g., fluorine atom, chlorine atom, or a bromine atom), an alkyl group having 1 to 6 carbon atoms (e.g., methyl group or ethyl group), a cyano group, a nitro group, a fluoroalkyl group having 1 to 6 carbon atoms (e.g., trifluoromethyl group or pentafluoroethyl group), an alkoxy group having 1 to 6 carbon atoms (e.g., methoxy group or ethoxy group), an alkylthio group having 1 to 6 carbon atoms (e.g., methylthio group or ethylthio group), a monosubstituted amino group (e.g., methylamino group, ethylamino group, or acetylamino group), a disubstituted amino group (e.g., dimethylamino group. diethylamino group, or phenylmethylamino group), or —C(=O)—O—R$^3$. Note that R$^3$ represents a hydrogen atom, or a substituted or unsubstituted alkyl group having 1 to 10 carbon atoms.

Examples of the substituted or unsubstituted alkyl group having 1 to 10 carbon atoms represented by R$^3$ include those mentioned above in connection with the substituted or unsubstituted alkyl group having 1 to 10 carbon atoms represented by R$^1$ and the like.

$R^X$ are identical to or different from each other, and an arbitrary C—R$^X$ that forms the ring is optionally substituted with a nitrogen atom. Specific examples of the compound represented by the formula (I) in which one or more C—R$^X$ are substituted with a nitrogen atom include, but are not limited to, the compounds shown below.

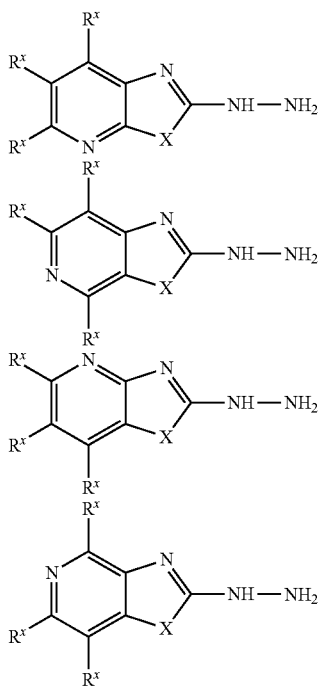

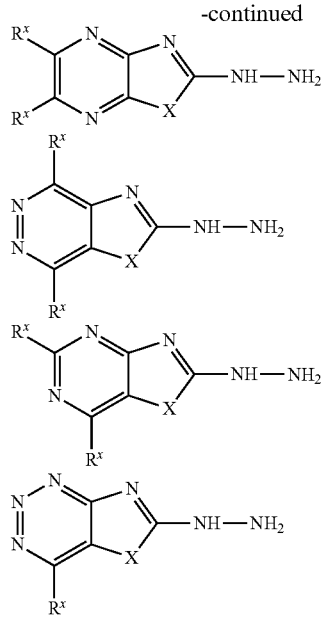

It is preferable that $R^X$ be an alkyl group having 1 to 6 carbon atoms or a hydrogen atom, and particularly preferably a hydrogen atom.

Hal in the formula (III) represents a chlorine atom, a bromine atom, or an iodine atom. Among these, a chlorine atom and a bromine atom are preferable since the advantageous effects of the invention can be more easily achieved.

R represents a substituted or unsubstituted organic group having 1 to 12 carbon atoms. The organic group having 1 to 12 carbon atoms is not particularly limited. Examples of the organic group having 1 to 12 carbon atoms include a hydrocarbon group such as an alkyl group having 1 to 12 carbon atoms, an alkenyl group having 2 to 12 carbon atoms, an alkynyl group having 2 to 12 carbon atoms, and an aryl group having 6 to 12 carbon atoms; a carboxyl group; an acid anhydride group; an amide group; and the like. Note that the number of carbon atoms of the organic group excludes the number of carbon atoms of a substituent.

Examples of the alkyl group having 1 to 12 carbon atoms include a methyl group, an ethyl group, an n-propyl group, an isopropyl group, an n-butyl group, a sec-butyl group, a t-butyl group, an n-pentyl group, an n-hexyl group, an n-heptyl group, an n-undecyl group, an n-dodecyl group, a 1-methylpentyl group, a 1-ethylpentyl group, and the like.

Examples of the alkenyl group having 2 to 12 carbon atoms include a vinyl group, an allyl group, an isopropenyl group, a butenyl group, and the like.

Examples of the alkynyl group having 2 to 12 carbon atoms include a propynyl group, a propargyl group, a butynyl group, and the like. Examples of the aryl group having 6 to 12 carbon atoms include a phenyl group, a 1-naphthyl group, a 2-naphthyl group, and the like.

Examples of a substituent that may substitute the hydrocarbon group include a cyano group; a nitro group; a hydroxyl group; a halogen atom such as a fluorine atom, a chlorine atom, and a bromine atom; an alkyl group having 1 to 6 carbon atoms, such as a methyl group and an ethyl group; an alkoxy group having 1 to 6 carbon atoms, such as a methoxy group, an ethoxy group, an n-propoxy group, an n-butoxy group, and a t-butoxy group; an alkoxy group having 1 to 6 carbon atoms that is substituted with an alkoxy group having 1 to 6 carbon atoms, such as a methoxymethoxy group, a methoxyethoxy group, and an ethoxyethoxy group; a substituted or unsubstituted aryl group such as a phenyl group, a 2-chlorophenyl group, a 3-methoxyphenyl group, a 4-methylphenyl group, and a 2,4-dimethylphenyl group; a cycloalkyl group having 3 to 8 carbon atoms, such as a cyclopropyl group, a cyclopentyl group, a cyclohexyl group, and a cycloheptyl group; a substituted amino group such as a methylamino group, an ethylamino group, an acetylamino group, and a dimethylamino group; and the like.

It is preferable that R be a substituted or unsubstituted hydrocarbon group having 1 to 12 carbon atoms, and more preferably a substituted or unsubstituted alkyl group having 1 to 12 carbon atoms.

In one embodiment of the invention, an alkali metal hydroxide or an alkaline-earth metal hydroxide is used as the base.

Examples of the alkali metal hydroxide include lithium hydroxide, sodium hydroxide, potassium hydroxide, and the like. Examples of the alkaline-earth metal hydroxide include calcium hydroxide, barium hydroxide, and the like. Magnesium hydroxide may also be used.

Among these, an alkali metal hydroxide is preferable, and sodium hydroxide and potassium hydroxide are particularly preferable.

The base is normally used in an amount of 1.0 to 3.0 equivalents, and preferably 1.0 to 2.0 equivalents. When the base is used in an amount within the above range, the target product can be obtained in high yield.

The reaction is effected in an aprotic polar solvent.

The term "aprotic polar solvent" used herein refers to a polar solvent that does not have a proton-donating capability. Examples of the aprotic polar solvent include a ketone-based solvent such as acetone, methyl ethyl ketone, 2-pentanone, 2-hexanone, methyl isobutyl ketone, and diisobutyl ketone; an ester-based solvent such as methyl acetate, ethyl acetate, propyl acetate, isopropyl acetate, butyl acetate, methyl propionate, and ethyl propionate; a sulfone-based solvent such as diethyl sulfone and diphenyl sulfone; a sulfoxide-based solvent such as dimethyl sulfoxide and diphenyl sulfoxide; an amine-based solvent such as N,N,N',N'-tetramethylethylenediamine and N,N-dimethylaniline; an amide-based solvent such as N,N-dimethylformamide, N,N-dimethylacetamide, and N-methylpyrrolidone; a urea-based solvent such as 1,3-dimethyl-2-imidazolidinone; a nitrile-based solvent such as acetonitrile, propionitrile, and benzonitrile; a nitro compound such as nitromethane and nitrobenzene; and the like. These solvents may be used either alone or in combination.

It is preferable to use a sulfoxide-based solvent, an amide-based solvent, or a nitrile-based solvent, more preferably N,N-dimethylformamide, N,N-dimethylacetamide, N-methylpyrrolidone, acetonitrile, 1,3-dimethyl-2-imidazolidinone, or dimethyl sulfoxide, since the advantageous effects of the invention can be more easily achieved.

The solvent may be used in an arbitrary amount. The solvent is normally used in an amount of 0.1 to 50 ml, preferably 0.5 to 20 ml, and more preferably 1 to 15 ml, per gram of the compound represented by the formula (I).

The compound (I) and the compound (III) are normally used in a molar ratio (compound (I):compound (III)) of 1:1 to 1:2, and preferably 1:1 to 1:1.3. When the compound (I) and the compound (III) are used in a ratio within the above range, the target product can be obtained in high yield.

The compound (I) and the compound (III) are reacted in the aprotic polar solvent in the presence of the base selected from an alkali metal hydroxide and an alkaline-earth metal hydroxide.

More specifically, the compound (I) and the compound (III) are reacted using a method ($\alpha$) that dissolves the compound (I) in the aprotic polar solvent, adds a specific amount of base (that is selected from an alkali metal hydroxide and an alkaline-earth metal hydroxide) and the compound (III) to the solution, and stirs the mixture, a method ($\beta$) that dissolves the compound (III) in the aprotic polar solvent, adds a specific amount of base (that is selected from an alkali metal hydroxide and an alkaline-earth metal hydroxide) and the compound (I) to the solution, and stirs the mixture, a method ($\gamma$) that dissolves the compound (I) and the compound (III) in the aprotic polar solvent, adds a specific amount of base (that is selected from an alkali metal hydroxide and an alkaline-earth metal hydroxide) to the solution, and stirs the mixture, or the like. It is preferable to use the method ($\alpha$).

When using the method ($\alpha$), a specific amount of base (that is selected from an alkali metal hydroxide and an alkaline-earth metal hydroxide) and the compound (III) may be simultaneously added to the solution prepared by dissolving the compound (I) in the aprotic polar solvent, or a specific amount of base (that is selected from an alkali metal hydroxide and an alkaline-earth metal hydroxide) may be added to the solution prepared by dissolving the compound (I) in the aprotic polar solvent, and the compound (III) may be added to the resulting mixture.

The base (that is selected from an alkali metal hydroxide and an alkaline-earth metal hydroxide) may be added to the reaction mixture in a solid state, or a solution (suspension) prepared by dissolving (suspending) the base (that is selected from an alkali metal hydroxide and an alkaline-earth metal hydroxide) in the aprotic polar solvent may be added to the reaction mixture.

The compound (III) may be added directly to the reaction mixture, or a solution prepared by dissolving the compound (III) in the aprotic polar solvent may be added to the reaction mixture.

The reaction temperature is normally set within the range from −10° C. to the boiling point of the solvent, and preferably 0 to 60° C. The reaction time is determined taking account of the reaction scale, but is normally set to several minutes to several hours.

The reaction is preferably effected in an inert atmosphere (e.g., nitrogen stream).

After completion of the reaction, the target product may be isolated by performing a post-treatment operation normally employed in synthetic organic chemistry. Note that it is preferable that the method according to one embodiment of the invention include adding a protic solvent to the reaction mixture to effect direct crystallization. When direct crystallization is effected without purification, a high-purity target product can be easily obtained in high yield.

The protic solvent is not particularly limited as long as the protic solvent is a poor solvent for the target 1,1-disubstituted hydrazine compound. Examples of the protic solvent include water; a monohydric alcohol such as ethanol, propanol, butanol, hexanol, cyclopentanol, cyclohexanol, and benzyl alcohol; a polyhydric alcohol such as ethylene glycol, propylene glycol, and glycerol; an oxyalcohol compound such as methyl cellosolve and dimethoxypropanol; and the like. It is particularly preferable to use water as the protic solvent.

The structure of the target product may be identified by measurement/elemental analysis (e.g., NMR spectrometry, IR spectrometry, or mass spectrometry), and the like.

The method according to one embodiment of the invention can produce the target 1,1-disubstituted hydrazine compound in high yield with high reaction selectivity using the compound (I) that is readily available as a raw material while using an inexpensive reagent.

EXAMPLES

The invention is further described below by way of examples. Note that the invention is not limited to the following examples. The conversion rate and the reaction selectivity were calculated as described below.

Conversion Rate

The conversion rate was calculated using the following expression.

Conversion rate=100−{unreacted 1-substituted hydrazine/1-substituted hydrazine subjected to reaction)×100}

Reaction Selectivity

The reaction selectivity was calculated using the following expression.

Reaction selectivity={amount of 1,1-disubstituted product/(amount of 1,1-disubstituted product+amount of 1,2-disubstituted product)}×100

Example 1

Synthesis of Compound 1

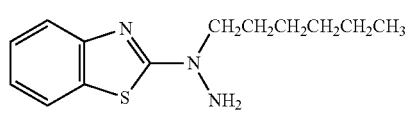

Compound 1

A three-necked reactor equipped with a thermometer was charged with 5.00 g (30.3 mmol) of 2-hydrazinobenzothiazole and 40 ml of N,N-dimethylformamide under a nitrogen stream to prepare a homogeneous solution. After the addition of 2.55 g (45.4 mmol) of potassium hydroxide and 6.00 g (36.3 mmol) of 1-bromohexane to the solution, the mixture was stirred at 25° C. for 2 hours. After completion of the reaction, the reaction mixture was cooled to 5° C., and 40 ml of water was added to the reaction mixture to precipitate a solid, which was filtered off. The solid was washed with 10 ml of water and 25 ml of n-heptane, and dried using a vacuum dryer to obtain 6.42 g of a compound 1 as a white solid (conversion rate: 95.1%, reaction selectivity: 96.7%, yield: 85.0%).

The structure of the target product was identified by $^1$H-NMR.

$^1$H-NMR (500 MHz, CDCl$_3$, TMS, δ ppm): 7.60 (dd, 1H, J=1.0 Hz, 8.0 Hz), 7.53 (dd, 1H, J=1.0 Hz, 8.0 Hz), 7.27 (ddd, 1H, J=1.0 Hz, 8.0 Hz, 8.0 Hz), 7.06 (ddd, 1H, J=1.0 Hz, 8.0 Hz, 8.0 Hz), 4.22 (s, 2H), 3.74 (t, 2H, J=7.5 Hz), 1.69-1.76 (m, 2H), 1.29-1.42 (m, 6H), 0.89 (t, 3H, J=7.0 Hz)

Example 2

Synthesis of Compound 2

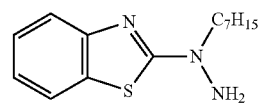

Compound 2

A three-necked reactor equipped with a thermometer was charged with 5.00 g (30.3 mmol) of 2-hydrazinobenzothiazole and 40 ml of N,N-dimethylformamide under a nitrogen stream to prepare a homogeneous solution. 1.82 g (45.4 mmol) of sodium hydroxide and 6.50 g (36.3 mmol) of 1-bromoheptane to the solution After completion of the reaction, the reaction mixture was cooled to 5° C., and 40 ml of water was added to the reaction mixture to precipitate a solid, which was filtered off. The solid was washed with 10 ml of water and 25 ml of n-heptane, and dried using a vacuum dryer to obtain 6.97 g of a compound 2 as a white solid (conversion rate: 94.6%, reaction selectivity: 95.7%, yield: 87.3%).

The structure of the target product was identified by $^1$H-NMR.

$^1$H-NMR (500 MHz, CDCl$_3$, TMS, δ ppm): 7.59 (dd, 1H, J=1.5 Hz, 8.0 Hz), 7.53 (dd, 1H, J=1.5 Hz, 8.0 Hz), 7.06-7.28 (m, 2H), 4.22 (s, 2H), 3.75 (t, 2H, J=7.0 Hz), 1.29-1.38 (m, 10H), 0.88 (t, 3H, J=7.0 Hz)

Example 3

Synthesis of Compound 3

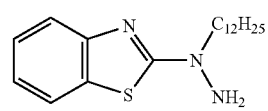

Compound 3

A three-necked reactor equipped with a thermometer was charged with 5.00 g (30.3 mmol) of 2-hydrazinobenzothiazole and 40 ml of dimethyl sulfoxide under a nitrogen stream to prepare a homogeneous solution. After the addition of 2.55 g (45.4 mmol) of potassium hydroxide and 9.05 g (36.3 mmol) of 1-bromododecane to the solution, the mixture was stirred at 25° C. for 3 hours. After completion of the reaction, the reaction mixture was cooled to 5° C., and 40 ml of water was added to the reaction mixture to precipitate a solid, which was filtered off. The solid was washed with 10 ml of water and 25 ml of n-heptane, and dried using a vacuum dryer to obtain 8.48 g of a compound 3 as a white solid (conversion rate: 91.3%, reaction selectivity: 97.7%, yield: 83.9%).

The structure of the target product was identified by $^1$H-NMR.

$^1$H-NMR (500 MHz, CDCl$_3$, TMS, δ ppm): 7.60 (dd, 1H, J=1.0 Hz, 8.0 Hz), 7.53 (dd, 1H, J=1.0 Hz, 8.0 Hz), 7.27 (ddd, 1H, J=1.0 Hz, 7.5 Hz, 8.0 Hz), 7.06 (ddd, 1H, J=1.0 Hz, 7.5 Hz, 8.0 Hz), 4.22 (s, 2H), 3.74 (t, 2H, J=7.5 Hz), 1.73 (tt, 2H, J=7.5 Hz, 7.5 Hz), 1.41-1.25 (m, 18H), 0.88 (t, 3H, J=7.0 Hz)

Example 4

Synthesis of Compound 4

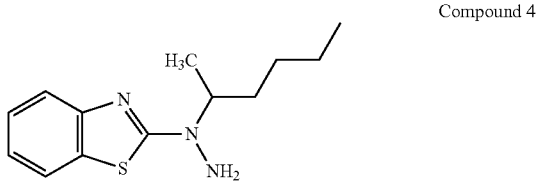 [SMILES: CCCCC(C)N(N)c1nc2ccccc2s1]

Compound 4

A three-necked reactor equipped with a thermometer was charged with 5.00 g (30.3 mmol) of 2-hydrazinobenzothiazole and 40 ml of dimethyl sulfoxide under a nitrogen stream to prepare a homogeneous solution. After the addition of 2.55 g (45.4 mmol) of potassium hydroxide and 5.99 g (36.3 mmol) of 1-bromohexane to the solution, the mixture was stirred at 25° C. for 2 hours. After completion of the reaction, the reaction mixture was cooled to 5° C., and 40 ml of water was added to the reaction mixture to precipitate a solid, which was filtered off. The solid was washed with 10 ml of water and 25 ml of n-heptane, and dried using a vacuum dryer to obtain 6.39 g of a compound 4 as a white solid (conversion rate: 92.3%, reaction selectivity: 96.6%, yield: 84.5%).

The structure of the target product was identified by $^1$H-NMR.

$^1$H-NMR (500 MHz, CDCl$_3$, TMS, δ ppm): 7.59 (dd, 1H, J=1.0 Hz, 8.0 Hz), 7.52 (dd, 1H, J=1.0 Hz, 8.0 Hz), 7.24-7.30 (m, 1H), 7.05 (ddd, 1H, J=1.0 Hz, 8.0 Hz, 8.0 Hz), 3.97 (s, 2H), 1.47-1.74 (m, 3H), 1.20-1.41 (m, 7H), 0.89 (t, 3H, J=5.5 Hz)

Example 5

Synthesis of Compound 5

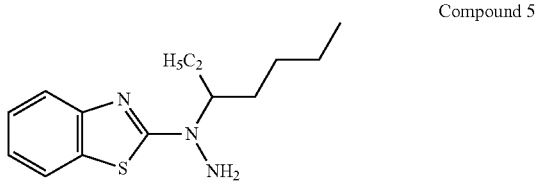

Compound 5

A three-necked reactor equipped with a thermometer was charged with 5.00 g (30.3 mmol) of 2-hydrazinobenzothiazole and 40 ml of acetonitrile under a nitrogen stream to prepare a homogeneous solution. After the addition of 1.82 g (45.4 mmol) of sodium hydroxide and 6.50 g (36.3 mmol) of 3-bromoheptane to the solution, the mixture was stirred at 25° C. for 2 hours. After completion of the reaction, the reaction mixture was cooled to 5° C., and 40 ml of water was added to the reaction mixture to precipitate a solid, which was filtered off. The solid was washed with 10 ml of water and 25 ml of n-heptane, and dried using a vacuum dryer to obtain 6.80 g of a compound 5 as a white solid (conversion rate: 93.0%, reaction selectivity: 95.5%, yield: 85.2%).

The structure of the target product was identified by $^1$H-NMR.

$^1$H-NMR (500 MHz, CDCl$_3$, TMS, δ ppm): 7.58 (dd, 1H, J=1.0 Hz, 7.5 Hz), 7.51 (dd, 1H, J=1.0 Hz, 7.5 Hz), 7.27 (ddd, 1H, J=1.0 Hz, 7.5 Hz, 7.5 Hz), 7.04 (ddd, 1H, J=1.0 Hz, 7.5 Hz, 7.5 Hz), 3.94 (s, 2H), 1.48-1.72 (m, 5H), 1.18-1.41 (m, 4H), 0.91 (t, 3H, J=7.5 Hz), 0.86 (t, 3H, J=7.5 Hz)

Example 6

Synthesis of Compound 6

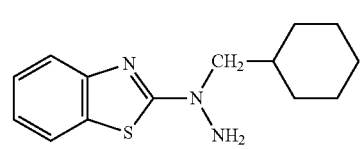

Compound 6

A three-necked reactor equipped with a thermometer was charged with 5.00 g (30.3 mmol) of 2-hydrazinobenzothiazole and 40 ml of 1,3-dimethyl-2-imidazolidinone under a nitrogen stream to prepare a homogeneous solution. After the addition of 1.82 g (45.4 mmol) of sodium hydroxide and 6.43 g (36.3 mmol) of (bromomethyl)cyclohexane to the solution, the mixture was stirred at 25° C. for 4 hours. After completion of the reaction, the reaction mixture was cooled to 5° C., and 40 ml of water was added to the reaction mixture to precipitate a solid, which was filtered off. The solid was washed with 10 ml of water and 25 ml of n-heptane, and dried using a vacuum dryer to obtain 6.66 g of a compound 6 as a white solid (conversion rate: 91.3%, reaction selectivity: 95.6%, yield: 84.1%).

The structure of the target product was identified by $^1$H-NMR.

$^1$H-NMR (400 MHz, CDCl$_3$, TMS, δ ppm): 7.58 (d, 1H, J=8.5 Hz), 7.51 (d, 1H, J=8.1 Hz), 7.26 (dd, 1H, J=7.0 Hz, 8.1 Hz), 7.04 (dd, 1H, J=7.0 Hz, 8.1 Hz), 4.24 (s, 2H), 3.59 (d, 2H, J=7.4 Hz), 1.84-1.92 (m, 1H), 1.67-1.77 (m, 5H), 1.16-1.29 (m, 3H), 1.02-1.13 (m, 2H)

Example 7

Synthesis of Compound 7

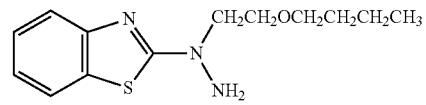

Compound 7

A three-necked reactor equipped with a thermometer was charged with 5.00 g (30.3 mmol) of 2-hydrazinobenzothiazole and 40 ml of N-methylpyrrolidone under a nitrogen stream to prepare a homogeneous solution. After the addition of 2.55 g (45.5 mmol) of potassium hydroxide and 4.96 g (36.3 mmol) of butyl 2-chloroethyl ether to the solution, the mixture was stirred for 2 hours. After completion of the reaction, the reaction mixture was cooled to 5° C., and 40 ml of water was added to the reaction mixture to precipitate a solid, which was filtered off at 5° C. The solid was washed with 10 ml of water and 25 ml of n-heptane, and dried using a vacuum dryer to obtain 6.73 g of a compound 7 as a white solid (conversion rate: 90.8%, reaction selectivity: 94.4%, yield: 83.7%).

The structure of the target product was identified by $^1$H-NMR.

$^1$H-NMR (500 MHz, CDCl$_3$, TMS, δ ppm): 7.61 (dd, 1H, J=1.0 Hz, 8.0 Hz), 7.50 (dd, 1H, J=1.0 Hz, 8.0 Hz), 7.27-7.29 (m, 1H), 7.04-7.08 (m, 1H), 4.70 (s, 2H), 4.01 (t, 2H, J=5.0 Hz), 3.82 (t, 2H, J=5.0 Hz), 3.44 (t, 2H, J=7.0 Hz), 1.52-1.57 (m, 2H), 1.31-1.39 (m, 2H), 0.90 (t, 3H, J=7.0 Hz)

Example 8

Synthesis of Compound 8

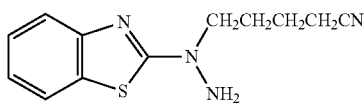

Compound 8

A three-necked reactor equipped with a thermometer was charged with 5.00 g (30.3 mmol) of 2-hydrazinobenzothiazole and 40 ml of N-methylpyrrolidone under a nitrogen stream to prepare a homogeneous solution. After the addition of 1.82 g (45.4 mmol) of sodium hydroxide and 5.88 g (36.3 mmol) of 5-bromovaleronitrile to the solution, the mixture was stirred at 25° C. for 3 hours. After completion of the reaction, the reaction mixture was cooled to 5° C., and 40 ml of water was added to the reaction mixture to precipitate a solid, which was filtered off. The solid was washed with 10 ml of water and 25 ml of n-heptane, and dried using a vacuum dryer to obtain 6.19 g of a compound 8 as a white solid (conversion rate: 91.1%, reaction selectivity: 97.7%, yield: 82.9%).

The structure of the target product was identified by $^1$H-NMR.

$^1$H-NMR (400 MHz, CDCl$_3$, TMS, δ ppm): 7.60 (d, 1H, J=7.8 Hz), 7.51 (d, 1H, J=8.1 Hz), 7.28 (dd, 1H, J=7.3 Hz, 7.8 Hz), 7.07 (dd, 1H, J=7.3 Hz, 7.8 Hz), 4.23 (s, 2H), 3.81 (t, 2H, J=6.9 Hz), 2.46 (t, 2H, J=7.1 Hz), 1.88-1.95 (m, 2H), 1.71-1.79 (m, 2H)

Example 9

Synthesis of Compound 9

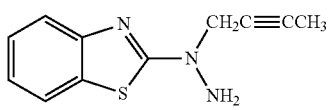

Compound 9

A three-necked reactor equipped with a thermometer was charged with 5.00 g (30.3 mmol) of 2-hydrazinobenzothiazole and 40 ml of N,N-dimethylformamide under a nitrogen stream to prepare a homogeneous solution. After the addition of 2.55 g (45.4 mmol) of potassium hydroxide and 4.83 g (36.3 mmol) of 1-bromo-2-butyne to the solution, the mixture was stirred at 25° C. for 2 hours. After completion of the reaction, the reaction mixture was cooled to 5° C., and 40 ml of water was added to the reaction mixture to precipitate a solid, which was filtered off. The solid was washed with 10 ml of water and 25 ml of heptane, and dried using a vacuum dryer to obtain 5.47 g of a compound 9 as a white solid (conversion rate: 94.1%, reaction selectivity: 95.7%, yield: 85.1%).

The structure of the target product was identified by $^1$H-NMR.

$^1$H-NMR (500 MHz, CDCl$_3$, TMS, δ ppm): 7.63 (dd, 1H, J=1.3 Hz, 7.8 Hz), 7.58 (dd, 1H, J=1.3 Hz, 7.8 Hz), 7.29 (ddd, 1H, J=1.3 Hz, 7.8 Hz, 7.8 Hz), 7.10 (ddd, 1H, J=1.3 Hz, 7.8 Hz, 7.8 Hz), 4.56 (q, 2H, J=2.5 Hz), 4.36 (s, 2H), 1.84 (t, 3H, J=2.5 Hz)

Example 10

Synthesis of Compound 10

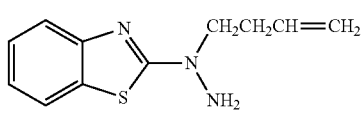

Compound 10

A three-necked reactor equipped with a thermometer was charged with 5.00 g (30.3 mmol) of 2-hydrazinobenzothiazole and 40 ml of N-methylpyrrolidone under a nitrogen stream to prepare a homogeneous solution. After the addition of 1.82 g (45.4 mmol) of sodium hydroxide and 4.90 g (36.3 mmol) of 4-bromo-1-butene to the solution, the mixture was stirred at 25° C. for 3 hours. After completion of the reaction, the reaction mixture was cooled to 5° C., and 40 ml of water was added to the reaction mixture to precipitate a solid, which was filtered off. The solid was washed with 10 ml of water and 25 ml of heptane, and dried using a vacuum dryer to obtain 6.00 g of a compound 10 as a white solid (conversion rate: 94.0%, reaction selectivity: 96.6%, yield: 84.9%).

The structure of the target product was identified by $^1$H-NMR.

$^1$H-NMR (500 MHz, CDCl$_3$, TMS, δ ppm): 7.60 (d, 1H, J=7.8 Hz), 7.54 (d, 1H, J=7.5 Hz), 7.30 (dd, 1H, J=7.8 Hz, 7.8 Hz), 7.07 (dd, 1H, J=7.5 Hz, 7.8 Hz), 5.89 (ddt, 1H, J=10.3 Hz, 17.0 Hz, 7.0 Hz), 5.18 (dd, 1H, J=1.5 Hz, 17.0 Hz), 5.09 (dd, 1H, J=1.5 Hz, 10.3 Hz), 4.27 (s, 2H), 3.86 (t, 2H, J=7.0 Hz), 2.53 (dt, 2H, J=7.0 Hz, 7.0 Hz)

Comparative Example 1

Synthesis of Compound 1

A reaction was effected (80° C., 6 hours) substantially in the same manner as in Example 1, except that 2-propanol was used as the solvent. After the addition of 20 ml of ethyl acetate, a post-treatment was performed substantially in the same manner as in Example 1 to obtain 2.67 g of the compound 1 (conversion rate: 68.3%, reaction selectivity: 56.4%, yield: 35.4%).

Comparative Example 2

Synthesis of Compound 1

A reaction was effected (80° C., 6 hours) substantially in the same manner as in Example 1, except that cyclopentyl methyl ether was used as the solvent. After the addition of 20 ml of ethyl acetate, a post-treatment was performed substantially in the same manner as in Example 1 to obtain 2.14 g of the compound 1 (conversion rate: 48.3%, reaction selectivity: 72.9%, yield: 28.3%).

Comparative Example 3

Synthesis of Compound 1

A reaction was effected (80° C., 6 hours) substantially in the same manner as in Example 1, except that toluene was used as the solvent. A post-treatment was performed substantially in the same manner as in Example 1 to obtain 0.26 g of the compound 1 (conversion rate: 12.1%, reaction selectivity: 59.4%, yield: 3.5%).

Comparative Example 4

Synthesis of Compound 1

A reaction was effected (80° C., 6 hours) substantially in the same manner as in Example 1, except that the solvent was not used. After the addition of 20 ml of ethyl acetate, a post-treatment was performed substantially in the same manner as in Example 1 to obtain 2.95 g of the compound 1 (conversion rate: 55.1%, reaction selectivity: 76.4%, yield: 39.1%).

Comparative Example 5

Synthesis of Compound 1

A reaction was effected (50° C., 8 hours) substantially in the same manner as in Example 1, except that a 40% potassium hydroxide aqueous solution was used as the base. A post-treatment was then performed substantially in the same manner as in Example 1 to obtain 2.61 g of the compound 1 (conversion rate: 72.5%, reaction selectivity: 66.7%, yield: 34.6%).

Comparative Example 6

Synthesis of Compound 1

A four-necked reactor equipped with a thermometer was charged with 2.00 g (12.1 mmol) of 2-hydrazinobenzothiazole and 20 ml of N,N-dimethylformamide under a nitrogen stream to prepare a homogeneous solution. After the addition of 8.36 g (60.5 mmol) of potassium carbonate and 3.08 g (14.5 mmol) of 1-iodohexane to the solution, the mixture was stirred at 50° C. for 7 hours. After completion of the reaction, the reaction mixture was cooled to 20° C., and added to 200 ml of water, followed by extraction with 300 ml of ethyl acetate. The ethyl acetate layer was dried over anhydrous sodium sulfate, and sodium sulfate was filtered off. Ethyl acetate was evaporated from the filtrate under reduced pressure using a rotary evaporator to obtain a yellow solid. The yellow solid was purified by silica gel column chromatography (n-hexane:ethyl acetate=75:25 (volume ratio (hereinafter the same))) to obtain 2.10 g of the compound 1 as a white solid (conversion rate: 92.1%, reaction selectivity: 73.3%, yield: 69.6%).

Comparative Example 7

Synthesis of Compound 2

A three-necked reactor equipped with a thermometer was charged with 2.00 g (12.1 mmol) of 2-hydrazinobenzothiazole and 30 ml of N,N-dimethylformamide under a nitrogen stream to prepare a solution. After the addition of 7.88 g (24.2 mmol) of cesium carbonate to the solution, the mixture was cooled to 25° C. After the dropwise addition of 3.28 g (14.5 mmol) of 1-iodoheptane to the mixture over 5 minutes, the mixture was stirred at 25° C. for 3 hours. After completion of the reaction, 200 ml of water was added to the reaction mixture, followed by extraction twice with 100 ml of ethyl acetate. The organic layer was dried over sodium sulfate, and concentrated using a rotary evaporator. The concentrate was purified by silica gel column chromatography (n-hexane:ethyl acetate=85:15) to obtain 1.81 g of the compound 2 as a white solid (conversion rate: 90.3%, reaction selectivity: 70.6%, yield: 56.9%).

Comparative Example 8

Synthesis of Compound 3

A four-necked reactor equipped with a thermometer was charged with 3.00 g (18.2 mmol) of 2-hydrazinobenzothiazole and 45 ml of N,N-dimethylformamide under a nitrogen stream to prepare a solution. After the addition of 11.9 g (36.4 mmol) of cesium carbonate and 6.45 g (21.8 mmol) of 1-iodododecane to the solution, the mixture was stirred at room temperature for 20 hours. After completion of the reaction, the reaction mixture was added to 200 ml of water, followed by extraction with 300 ml of ethyl acetate. The ethyl acetate layer was dried over anhydrous sodium sulfate, and sodium sulfate was filtered off. Ethyl acetate was evaporated from the filtrate under reduced pressure using a rotary evaporator to obtain a yellow solid. The yellow solid was purified by silica gel column chromatography (toluene:ethyl acetate=95:5) to obtain 2.93 g of the compound 3 as a white solid (conversion rate: 89.0%, reaction selectivity: 72.2%, yield: 48.3%).

Comparative Example 9

Synthesis of Compound 4

A three-necked reactor equipped with a thermometer was charged with 2.00 g (12.1 mmol) of 2-hydrazinobenzothiazole and 30 ml of N,N-dimethylformamide under a nitrogen stream to prepare a solution. After the addition of 7.88 g (24.2 mmol) of cesium carbonate to the solution, the mixture was cooled to 0° C. After the dropwise addition of 2.39 g (14.5 mmol) of 2-bromohexane to the mixture over 5 minutes, the mixture was stirred at 25° C. for 3 hours. After completion of the reaction, 200 ml of water was added to the reaction mixture, followed by extraction twice with 100 ml of ethyl acetate. The organic layer was dried over sodium sulfate, and concentrated using a rotary evaporator. The concentrate was purified by silica gel column chromatography (n-hexane:ethyl acetate=93:7) to obtain 1.61 g of the compound 4 as a white solid (conversion rate: 90.2%, reaction selectivity: 63.5%, yield: 53.4%).

Comparative Example 10

Synthesis of Compound 5

A three-necked reactor equipped with a thermometer was charged with 2.00 g (12.1 mmol) of 2-hydrazinobenzothiazole and 30 ml of N,N-dimethylformamide under a nitrogen stream to prepare a solution. After the addition of 7.88 g (24.2 mmol) of cesium carbonate to the solution, the mixture was cooled to 0° C. After the dropwise addition of 2.60 g (14.5 mmol) of 3-bromoheptane to the mixture over 5 minutes, the mixture was stirred at 25° C. for 3 hours. After completion of the reaction, 200 ml of water was added to the reaction mixture, followed by extraction twice with 100 ml of ethyl acetate. The organic layer was dried over sodium sulfate, and concentrated using a rotary evaporator. The concentrate was purified by silica gel column chromatography (n-hexane:ethyl acetate=9:1) to obtain 1.80 g of the compound 5 as a white solid (conversion rate: 88.9%, reaction selectivity: 66.7%, yield: 56.4%).

Comparative Example 11

Synthesis of Compound 6

A four-necked reactor equipped with a thermometer was charged with 3.00 g (18.2 mmol) of 2-hydrazinobenzothiazole and 30 ml of N,N-dimethylformamide under a nitrogen stream to prepare a homogeneous solution. After the addition of 7.55 g (54.6 mmol) of potassium carbonate and 3.86 g (21.8 mmol) of (bromomethyl)cyclohexane to the solution, the mixture was stirred at 80° C. for 9 hours. After completion of the reaction, the reaction mixture was cooled to 20° C., and added to 300 ml of water, followed by extraction with 500 ml of ethyl acetate. The ethyl acetate layer was dried over anhydrous sodium sulfate, and sodium sulfate was filtered off. Ethyl acetate was evaporated from the filtrate under reduced pressure using a rotary evaporator to obtain a yellow solid. The yellow solid was purified by silica gel column chromatography (n-hexane:ethyl acetate=85:15) to obtain 2.36 g of the compound 6 as a white solid (conversion rate: 87.3%, reaction selectivity: 65.6%, yield: 49.7%).

Comparative Example 12

Synthesis of Compound 7

A three-necked reactor equipped with a thermometer was charged with 2.00 g (12.1 mmol) of 2-hydrazinobenzothiazole and 30 ml of N,N-dimethylformamide under a nitrogen stream to prepare a solution. After the addition of 7.88 g (24.2 mmol) of cesium carbonate to the solution, the mixture was cooled to 0° C. After the dropwise addition of 1.98 g (14.5 mmol) of butyl 2-chloroethyl ether to the mixture over 5 minutes, the mixture was stirred at 25° C. for 3 hours. After completion of the reaction, 200 ml of water was added to the reaction mixture, followed by extraction twice with 100 ml of ethyl acetate. The organic layer was dried over sodium sulfate, and concentrated using a rotary evaporator. The concentrate was purified by silica gel column chromatography (n-hexane:ethyl acetate=75:25) to obtain 1.70 g of the compound 7 as a white solid (conversion rate: 86.3%, reaction selectivity: 69.4%, yield: 53.0%).

Comparative Example 13

Synthesis of Compound 8

A four-necked reactor equipped with a thermometer was charged with 5.00 g (30.3 mmol) of 2-hydrazinobenzothiazole and 100 ml of N,N-dimethylformamide under a nitrogen stream to prepare a homogeneous solution. After the addition of 20.9 g (152 mmol) of potassium carbonate and 5.17 g (31.9 mmol) of 5-bromovaleronitrile to the solution, the mixture was stirred at 60° C. for 8 hours. After completion of the reaction, the reaction mixture was cooled to 20° C., and added to 500 ml of water, followed by extraction with 500 ml of ethyl acetate. The ethyl acetate layer was dried over anhydrous sodium sulfate, and sodium sulfate was filtered off. Ethyl acetate was evaporated from the filtrate under reduced pressure using a rotary evaporator to obtain a yellow solid. The yellow solid was purified by silica gel column chromatography (n-hexane:ethyl acetate=60:40) to obtain 3.41 g of the compound 8 as a white solid (conversion rate: 87.3%, reaction selectivity: 66.3%, yield: 45.7%).

The results of Examples 1 to 10 and Comparative Examples 1 to 13 are shown in Table 1.

Note that each solvent shown in Table 1 has the following meaning.
1: N,N-Dimethylformamide
2: Dimethyl sulfoxide
3: Acetonitrile
4: 1,3-Dimethyl-2-imidazolidinone
5: N-Methylpyrrolidone
6: 2-Propanol
7: Cyclopentyl methyl ether
8: Toluene
9: Water The symbol "*" shown in Table 1 indicates that the nitrogen atom is bonded.

TABLE 1

| | Compound (II) | | | Compound (I) | | Base | |
|---|---|---|---|---|---|---|---|
| | | | Equivalents | | | | Equivalents |
| | R | Hal | (eq) | RX | X | Type | (eq) |
| Example 1 | $C_6H_{13}$ | Br | 1.2 | H | S | KOH | 1.5 |
| Example 2 | $C_7H_{15}$ | Br | 1.2 | H | S | NaOH | 1.5 |
| Example 3 | $C_{12}H_{25}$ | Br | 1.2 | H | S | KOH | 1.5 |
| Example 4 | $CH(CH_3)C_4H_9$ | Br | 1.2 | H | S | KOH | 1.5 |
| Example 5 | $CH(C_2H_5)C_4H_9$ | Br | 1.2 | H | S | NaOH | 1.5 |
| Example 6 | 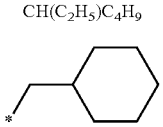 | Br | 1.2 | H | S | NaOH | 1.5 |
| Example 7 | $C_2H_4OC_4H_9$ | Cl | 1.2 | H | S | KOH | 1.5 |
| Example 8 | $C_4H_8CN$ | Br | 1.2 | H | S | NaOH | 1.5 |
| Example 9 | $CH_2C{=}CCH_3$ | Br | 1.2 | H | S | KOH | 1.5 |
| Example 10 | $CH_2CH_2CH{=}CH_2$ | Br | 1.2 | H | S | NaOH | 1.5 |

TABLE 1-continued

| | | | | | | | |
|---|---|---|---|---|---|---|---|
| Comparative Example 1 | C$_6$H$_{13}$ | I | 1.2 | H | S | KOH | 1.5 |
| Comparative Example 2 | C$_6$H$_{13}$ | I | 1.2 | H | S | KOH | 1.5 |
| Comparative Example 3 | C$_6$H$_{13}$ | I | 1.2 | H | S | KOH | 1.5 |
| Comparative Example 4 | C$_6$H$_{13}$ | I | 1.2 | H | S | KOH | 1.5 |
| Comparative Example 5 | C$_6$H$_{13}$ | I | 1.2 | H | S | KOH | 1.5 |
| Comparative Example 6 | C$_6$H$_{13}$ | I | 1.2 | H | S | K$_2$CO$_3$ | 5 |
| Comparative Example 7 | C$_7$H$_{15}$ | I | 1.2 | H | S | Cs$_2$CO$_3$ | 2 |
| Comparative Example 8 | C$_{12}$H$_{25}$ | I | 1.2 | H | S | Cs$_2$CO$_3$ | 2 |
| Comparative Example 9 | CH(CH$_3$)C$_4$H$_9$ | Br | 1.2 | H | S | Cs$_2$CO$_3$ | 2 |
| Comparative Example 10 | CH(C$_2$H$_5$)C$_4$H$_9$ | Br | 1.2 | H | S | Cs$_2$CO$_3$ | 2 |
| Comparative Example 11 | 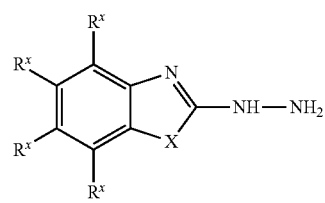 | Br | 1.2 | H | S | K$_2$CO$_3$ | 3 |
| Comparative Example 12 | C$_2$H$_4$OC$_4$H$_9$ | Cl | 1.2 | H | S | Cs$_2$CO$_3$ | 2 |
| Comparative Example 13 | C$_4$H$_8$CN | Br | 1.1 | H | S | K$_2$CO$_3$ | 5 |

| | Solvent | Reaction Temperature (° C.) | Reaction Time (h) | Conversion rate (%) | Reaction selectivity (%) | Isolated yield (%) |
|---|---|---|---|---|---|---|
| Example 1 | 1 | 25 | 2 | 95.1 | 96.7 | 85 |
| Example 2 | 1 | 25 | 2 | 94.6 | 95.7 | 87.3 |
| Example 3 | 1 | 25 | 3 | 91.3 | 97.7 | 83.9 |
| Example 4 | 1 | 25 | 2 | 92.3 | 96.6 | 84.5 |
| Example 5 | 3 | 25 | 2 | 93 | 95.5 | 85.2 |
| Example 6 | 4 | 25 | 4 | 91.3 | 95.6 | 84.1 |
| Example 7 | 5 | 25 | 2 | 90.8 | 94.4 | 83.7 |
| Example 8 | 5 | 25 | 3 | 91.1 | 97.7 | 82.9 |
| Example 9 | 1 | 25 | 2 | 94.1 | 95.7 | 85.1 |
| Example 10 | 5 | 25 | 3 | 94 | 96.6 | 84.9 |
| Comparative Example 1 | 6 | 80 | 6 | 68.3 | 56.4 | 35.4 |
| Comparative Example 2 | 7 | 80 | 6 | 48.3 | 72.9 | 28.3 |
| Comparative Example 3 | 8 | 80 | 6 | 12.1 | 59.4 | 3.5 |
| Comparative Example 4 | — | 80 | 6 | 55.1 | 76.4 | 39.1 |
| Comparative Example 5 | 1/9 | 50 | 8 | 72.5 | 66.7 | 34.6 |
| Comparative Example 6 | 1 | 50 | 7 | 92.1 | 73.3 | 69.6 |
| Comparative Example 7 | 1 | 25 | 3 | 90.3 | 70.6 | 56.9 |
| Comparative Example 8 | 1 | 25 | 20 | 89 | 72.2 | 48.3 |
| Comparative Example 9 | 1 | 25 | 3 | 90.2 | 63.5 | 53.4 |
| Comparative Example 10 | 1 | 25 | 3 | 88.9 | 66.7 | 56.4 |
| Comparative Example 11 | 1 | 80 | 9 | 87.3 | 65.6 | 49.7 |
| Comparative Example 12 | 1 | 25 | 3 | 86.3 | 69.4 | 53 |
| Comparative Example 13 | 1 | 60 | 8 | 87.3 | 66.3 | 45.7 |

As shown in Table 1, the target product was obtained in Examples 1 to 10 in high yield while achieving a high conversion rate and high reaction selectivity.

In Comparative Examples 6 to 13 in which a hydroxide of an alkali metal or the like was not used as the base, the reaction selectivity and the isolated yield of the target product were low. In Comparative Examples 1 to 5 in which an aprotic polar solvent was not used as the solvent, the conversion rate, the reaction selectivity, and the isolated yield were low.

The invention claimed is:

1. A method for producing a 1,1-disubstituted hydrazine compound comprising reacting a hydrazino compound represented by a formula (I) with a compound represented by a formula (III): R-Hal in an aprotic polar solvent in the presence of a base selected from an alkali metal hydroxide and alkaline-earth metal hydroxide in an amount of 1.0 to 3.0 equivalents based on the hydrazino compound,

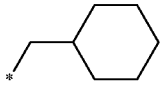 [SMILES: *CC1CCCCC1]

wherein Hal represents a chlorine atom, a bromine atom, or an iodine atom, and R represents a substituted or unsubstituted organic group having 1 to 12 carbon atoms, wherein X represents an oxygen atom, a sulfur atom, —CH$_2$—, —CHR$^1$—, —CR$^1$R$^2$—, or —NR$^1$—, wherein each of R$^1$ and R$^2$ independently represents a hydrogen atom, or a substituted or unsubstituted alkyl group having 1 to 10 carbon atoms, and wherein each of $R^x$ represents a hydrogen atom, a halogen atom, an alkyl group having 1 to 6 carbon atoms, a cyano group, a nitro group, a fluoroalkyl group having 1 to 6 carbon atoms, an alkoxy group having 1 to 6 carbon atoms, an alkylthio group having 1 to 6 carbon atoms, a monosubstituted amino group, a disubstituted amino group, or —C(=O)—O—$R^3$, wherein $R^3$ represents a hydrogen atom, or a substituted or unsubstituted alkyl group having 1 to 10 carbon atoms, provided that $R^x$ are identical to or different from each other, and an arbitrary C—$R^x$ that forms the ring is optionally substituted with a nitrogen atom, the 1,1-disubstituted hydrazine compound being represented by a formula (II),

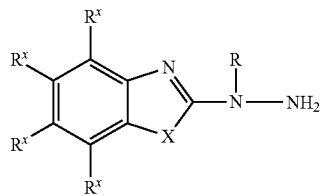

(II)

wherein X, R, and $R^x$ are the same as defined above.

2. The method according to claim 1, further comprising adding a protic solvent to a reaction mixture obtained by the reaction to effect direct crystallization.

3. The method according to claim 2, wherein the protic solvent is water.

4. The method according to claim 1, wherein the compound represented by the formula (I) is the compound represented by the formula (I) in which each of $R^x$ is a hydrogen atom.

5. The method according to claim 1, wherein the compound represented by the formula (I) is the compound represented by the formula (I) in which X is a sulfur atom.

6. The method according to claim 1, wherein the compound represented by the formula (III): R-Hal is the compound represented by the formula (III) in which R is a substituted or unsubstituted alkyl group having 1 to 12 carbon atoms.

7. The method according to claim 1, wherein the base is an alkali metal hydroxide.

8. The method according to claim 1, wherein the base is sodium hydroxide or potassium hydroxide.

9. The method according to claim 1, wherein the base is used in an amount of 1.0 to 2.0 equivalents based on the hydrazino compound.

10. The method according to claim 1, wherein the aprotic polar solvent is at least one aprotic polar solvent selected from a group consisting of N,N-dimethylformamide, N,N-dimethylacetamide, N-methylpyrrolidone, acetonitrile, 1,3-dimethyl-2-imidazolidinone, and dimethyl sulfoxide.

* * * * *